US00PP09151P

United States Patent [19]

Enthoven

[11] Patent Number: Plant 9,151

[45] Date of Patent: May 30, 1995

[54] GERANIUM PLANT NAMED MERIONE

[75] Inventor: Adrianus W. M. Enthoven, Wateringen, Netherlands

[73] Assignee: Enthoven Breeding B.V., Wateringen, Netherlands

[21] Appl. No.: 197,347

[22] Filed: Feb. 16, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 5,940 4/1987 Sehumann ..... Plt./87.12

P.P. 7,609 7/1991 Winner ..... Plt./87.12

*Primary Examiner*—James R. Feyrer

*Attorney, Agent, or Firm*—Foley & Lardner

[57] ABSTRACT

A new and distinct cultivar of geranium named Merione, particularly characterized by the combined features of red flowers that are semi-double, elliptic flower buds, early and equal flowering, large inflorescences with many flowers that open at the same time, flower stalks are long enough to grow above the plant, compact plant growth habit growing low and wide, green foliage with a light zone of red-brown color and leaf margins that are slightly incised, double crenated and wavy.

3 Drawing Sheets

The present invention comprises a new and distinct cultivar of geranium, botanically known as *Pelargonium zonale*, and hereinafter referred to by the cultivar name Merione.

Merione is a product of a planned breeding program which had the objective of creating new geranium cultivars with semi-double flower form, compact habit, fast rooting, good tolerance to Botrytis, superior weather resistance and little need for growth regulators.

Merione was originated from a hybridization made by the inventor in a controlled breeding program in Wateringen, The Netherlands in 1987. The female parent was an unnamed and proprietary Enthoven seedling, characterized by its compact growth. The male parent of Merione was an unnamed and proprietary Enthoven seedling, characterized by its weather resistance.

Merione was discovered and selected as one flowering plant within the progeny of the stated cross by Adrianus W. M. Enthoven in June 1988 in a controlled environment in Wateringen, The Netherlands.

The first act of asexual reproduction of Merione was accomplished when vegetative cuttings were taken from the initial selection in August 1988 in a controlled environment in Wateringen, The Netherlands under the supervision of Adrianus W. M. Enthoven.

Horticultural examination of selected units initiated in the spring and summer of 1989, and continuing thereafter, has demonstrated that the combination of characteristics as herein disclosed for Merione are firmly fixed and are retained through successive generations of asexual reproduction.

Merione has not been observed under all possible environmental conditions. The phenotype may vary with variations in environment such as temperature, light intensity and day length, without, however, any variation in genotype.

The following measurments, and comparisons described plants grown in Wateringen, The Netherlands under greenhouse and outdoor conditions which approximate those generally used in commercial practice.

The following traits have been repeatedly observed and are determined to be basic characteristics of Merione, which in combination distinguish this geranium as a new and distinct cultivar:

1. The plant has a compact growth habit growing low and wide.
2. The foliage is green (upper side of leaf is R.H.S. 138A–B) with a light zone (R.H.S. 137B) and with a pale red-brown overcolor on the outer zone.
3. The leaf margins are slightly incised, double crenated and wavy.
4. The leaf stalks are green and sturdy.
5. The flower stalks are long enough to grow above the plant.
6. The inflorescence is large with many flowers that open at the same time.
7. The flowers are large in diameter and the little flower stalks are very long.
8. The flower buds are elliptic in shape.
9. The flowers are red in color and are semi-double.
10. Flowering occurs early and equally with new flower buds forming after each pair of leaves develop.
11. Growth of the plants are controlled so that growth regulators are almost not needed. The plants at matunty are compact with a diameter and height equal to approximately 205 mm.
12. The plant is rather rain resistant because the flowers of the inflorescense have a long flower stalk.

Of the many commercial cultivars known to the present inventor, the most similar in comparison to Merione is the cultivar Isabelle, disclosed in U.S. Plant Pat. No. 7,080. Reference is made to Chart A which compares certain characteristics of Merione to those same characteristics of Isabelle. Among the characteristics that distinguish Merione from Isabelle is that Merione has a double crenated and slightly incised leaf margin, and a compact growth habit. The leaf and petal color and leaf zonation of Merione and Isabelle also differ.

The accompanying color photographic drawings show typical flower and foliage characteristics of Merione, with colors being as true as possible with illustrations of this type.

Sheet 1 is a side view of Merione grown in a 10.5 cm pot for approximately 8 weeks showing the foliage, flower stalks and inflorescences.

Sheet 2 is a close-up view of the upper and lower sides of a typical leaf from Merione.

Sheet 3 is a close-up view of a typical flower from Merione showing the flowers from the top and bottom.

In the following description color references are made to The Royal Horticultural Society Colour Chart (R.H.S.) and Horticultural Color Chart (H.C.C.). The color values were determined between 2:10 and 2:30 p.m. on Jul. 31, 1989 under 21,500 Klux light intensity at Wateringen, The Netherlands.

Classification:

*Botanical.*—A hybrid of the genus *Pelargonium zonale* cv. Merione.

*Commercial.*—Zonal geranium.

INFLORESCENCE

A. Umbel:

*Average diameter.*—Indoor: 132 mm.

*Average depth.*—Indoor: 92 mm.

*Peduncle length.*—Indoor: 174 mm.

*Pedicel length.*—Indoor: 37 mm.

*Pedicel color.*—Reddish green becoming dark red near top.

B. Corolla:

*Average diameter.*—Indoor: 48 mm.

*Form.*—Semi-double approximately 3 petaloids and 5 petals.

*Color (general tonality at a distance of three meters-*.—R.H.S. 43 A, H.C.C. 719.

*Color (main body, upper surface).*—R.H.S. 43 A, H.C.C. 719.

*Color (near margin upper face).*—R.H.S. 43 A, H.C.C. 719.

*Color (lower side of petal).*—R.H.S. 46 D, H.C.C. 719/3.

*Diameter lower petals.*—24 mm.

*Length lower petals.*—38 mm.

*Diameter upper petals.*—19 mm.

*Length upper petals.*—29 mm.

*Petal shape.*—Obovate.

*Sepal color.*—Green with dark-red veins at the bottom.

C. Bud:

*Shape.*—Elliptic.

*Color.*—Slightly lighter than corolla.

*Pedical.*—Red.

D. Reproductive organs:

*Androecium.*—7–9 anthers.

*Gynoecium.*—4–5 stigma.

E. Spring flowering:

*Response period.*—In Wateringen, The Netherlands in 1989, 60% of plants with at least 1 flower opened 13 weeks after planting of unrooted cuttings.

F. Outdoor flower production: The flower count in 1989 in Wateringen, The Netherlands was between 48–53 flowers per plant from June through October observation period.

G. Durability: 100% shatter resistance.

PLANT

A. Foliage:

*Form.*—Kidney shaped with open base.

*Margin.*—Bicrenate.

*Color.*—Medium green (upper side R.H.S. 138A–B).

*Zonation.*—Present (R.H.S. 137B).

*Length.*—38 mm.

*Diameter.*—78 mm.

B. General appearance and form:

*Internode length.*—30 mm.

*Branching pattern.*—An average of 5.7 branches per plant.

*Height.*—205 mm.

C. Tolerance to Botrytis: Good.

CHART A

COMPARISON OF MERIONE AND ISABELLE

| | Merione | Isabelle |
|---|---|---|
| Form | Compact | Upright |
| Height | 23.5 cm | 25–30 cm from surface of medium |
| Leaf margin | double crenated and wavy, slightly incised | crenate |
| Leaf color | main color medium green | outside margin 137B, center 137C |
| Leaf zonation | reddish brown | 187C |
| Petal color | Top-red group 43A Bottom-red group 46D | Top-red group 40A Bottom-red group 43B |

I claim:

1. A new and distinct cultivar of geranium plant named Merione, as illustrated and described.

* * * * *

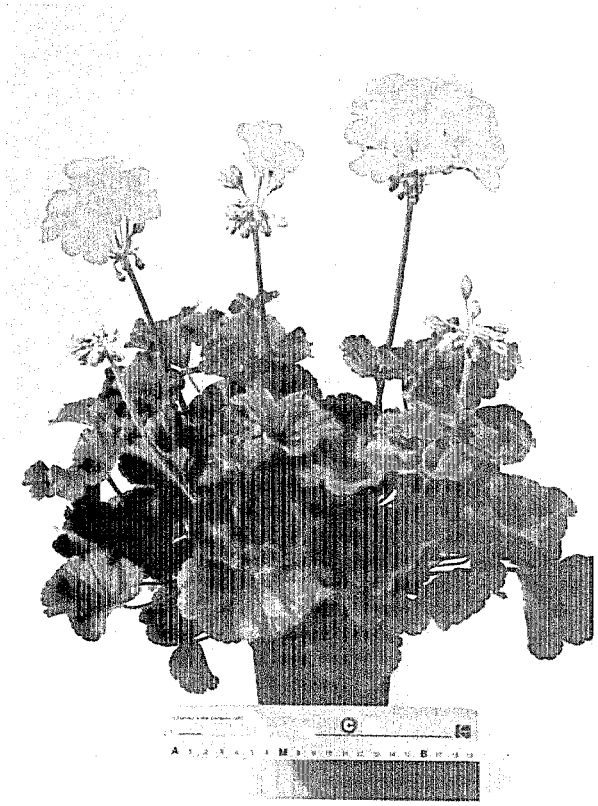

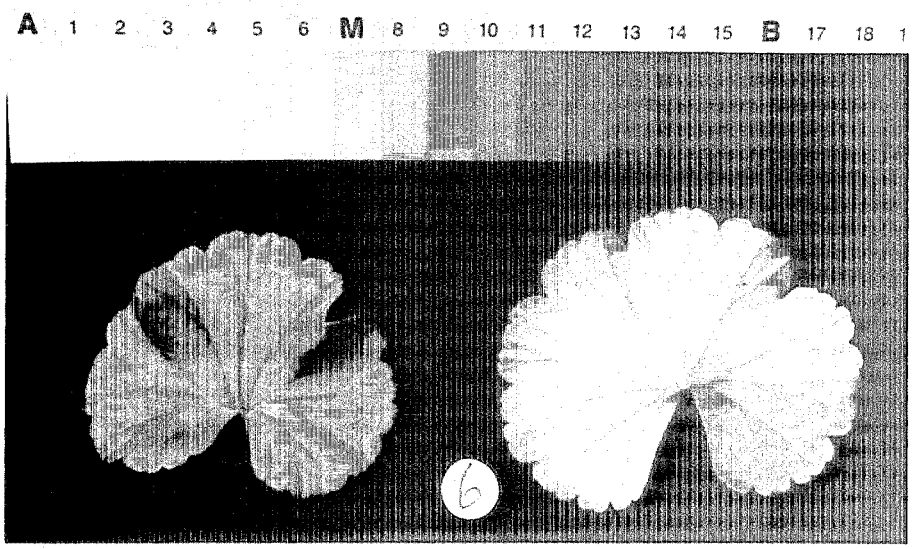
A 1 2 3 4 5 6 M 8 9 10 11 12 13 14 15 B 17 18 1
6

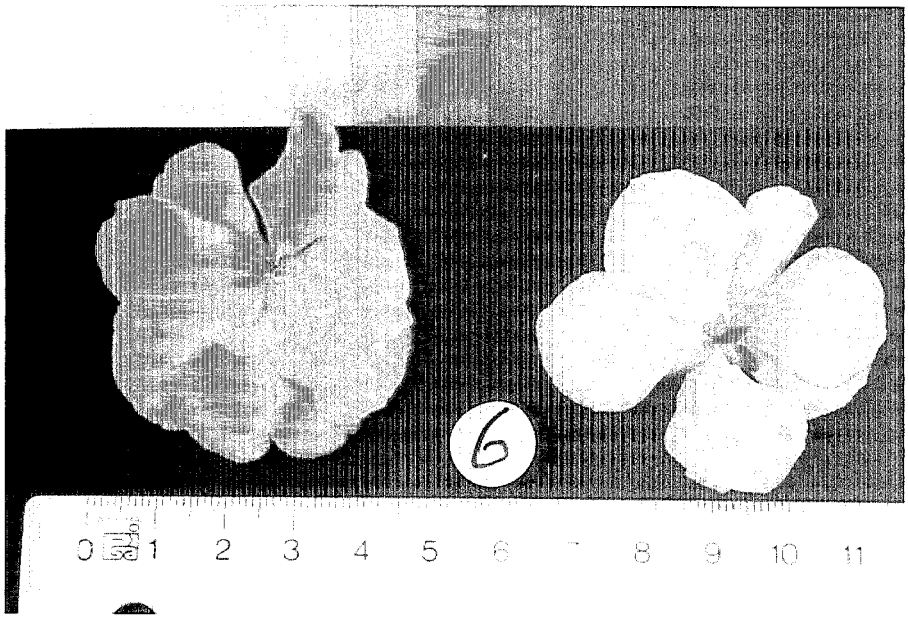
6
0 1 2 3 4 5 8 9 10 11